United States Patent
Grass et al.

(10) Patent No.: US 10,561,383 B2
(45) Date of Patent: Feb. 18, 2020

(54) IMAGING SYSTEM FOR IMAGING AN ELONGATED REGION OF INTEREST OF AN OBJECT

(71) Applicant: KONINKLIJKE PHILIPS N.V., Eindhoven (NL)

(72) Inventors: Michael Grass, Buchholz in der Nordheide (DE); Eberhard Sebastian Hansis, Hamburg (DE); Dirk Schäfer, Hamburg (DE); Tobias Klinder, Uelzen (DE); Christian Haase, Hamburg (DE); Hanno Heyke Homann, Hannover (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 202 days.

(21) Appl. No.: 15/535,667

(22) PCT Filed: Dec. 17, 2015

(86) PCT No.: PCT/EP2015/080272
§ 371 (c)(1),
(2) Date: Jun. 14, 2017

(87) PCT Pub. No.: WO2016/097174
PCT Pub. Date: Jun. 23, 2016

(65) Prior Publication Data
US 2017/0340299 A1    Nov. 30, 2017

(30) Foreign Application Priority Data

Dec. 18, 2014    (EP) ..................................... 14198831

(51) Int. Cl.
*A61B 6/08*    (2006.01)
*A61B 6/06*    (2006.01)
(Continued)

(52) U.S. Cl.
CPC .............. *A61B 6/4441* (2013.01); *A61B 6/03* (2013.01); *A61B 6/504* (2013.01)

(58) Field of Classification Search
CPC ........... A61B 6/00; A61B 6/4441; A61B 6/06; A61B 6/4291; A61B 6/54; G01N 23/04
See application file for complete search history.

(56) References Cited

U.S. PATENT DOCUMENTS

| 2001/0014140 A1 | 8/2001 | Proksa et al. |
| 2006/0023830 A1 | 2/2006 | Schomberg |

(Continued)

FOREIGN PATENT DOCUMENTS

| DE | 102006002907 A1 | 7/2007 |
| DE | 102011089178 A1 | 6/2013 |

(Continued)

OTHER PUBLICATIONS

Kohler et al: "A Fast and Efficient Method for Sequential Cone-Beam Tomography" Med. Phys. 28 (11), Nov. 2001, pp. 2318-2327.

(Continued)

Primary Examiner — Don K Wong

(57) ABSTRACT

The invention relates to an imaging system (10) for imaging an elongated region of interest of an object, an imaging method for imaging an elongated region of interest of an object, a computer program element for controlling such system for performing such method and a computer readable medium having stored such computer program element. The imaging system (10) comprises an acquisition unit (11) and a processing unit (13). The acquisition unit (11) is a C-arm acquisition unit and configured to acquire first image data of the object to be imaged with a first imaging parameter. The acquisition unit (11) is further configured to acquire second, different image data of an object to be imaged with a second imaging parameter. The second geometric imaging parameter is defined based on object specific data for the volume (Continued)

data to be aligned with the elongated region of interest of the object to be imaged. The processing unit (13) is configured to combine the first and second image data into volume data.

14 Claims, 4 Drawing Sheets

(51) Int. Cl.
*A61B 6/00* (2006.01)
*A61B 6/03* (2006.01)

(56) References Cited

U.S. PATENT DOCUMENTS

| | | |
|---|---|---|
| 2007/0140427 A1 | 6/2007 | Jensen |
| 2011/0075798 A1 | 3/2011 | Boese |
| 2012/0183120 A1 | 7/2012 | Tomoe |
| 2012/0257714 A1 | 10/2012 | Graumann |
| 2014/0081131 A1 | 3/2014 | Kyriakou |
| 2014/0321612 A1 | 10/2014 | Schafer |
| 2016/0054239 A1* | 2/2016 | Schlecht ............... A61B 6/032 378/11 |

FOREIGN PATENT DOCUMENTS

| | | |
|---|---|---|
| DE | 102012216652 A1 | 3/2014 |
| EP | 1263216 A1 | 12/2002 |
| WO | 2006070328 A1 | 7/2006 |

OTHER PUBLICATIONS

Yu et al: "FDK-Type Reconstruction Algorithms for the Reverse Helical Trajectory"; 2011 IEEE Nuclear Science Symposium Conference Record, pp. 3980-39845.

* cited by examiner

IMAGING SYSTEM FOR IMAGING AN ELONGATED REGION OF INTEREST OF AN OBJECT

CROSS-REFERENCE TO PRIOR APPLICATIONS

This application is the U.S. National Phase application under 35 U.S.C. § 371 of International Application No. PCT/EP2015/080272, filed on Dec. 17, 2015, which claims the benefit of European Patent Application No. 14198831.1, filed on Dec. 18, 2014. These applications are hereby incorporated by reference herein.

FIELD OF THE INVENTION

The invention relates to an imaging system for imaging an elongated region of interest of an object, an imaging method for imaging an elongated region of interest of an object, a computer program element for controlling such system for performing such method and a computer readable medium having stored such computer program element.

BACKGROUND OF THE INVENTION

In C-arm X-ray systems, the C-arm moves an X-ray tube and an X-ray detector freely around the patient. Thereby, a continuous imaging of an object during interventional procedures is enabled. WO 2006/070328 (A1) hereto discloses a medical three-dimensional X-ray imaging device comprising a C-shaped arm that can revolve around an axis of rotation through an object to be imaged. An X-ray source is attached to one end of the C-shaped arm, and an X-ray detector for receiving X-rays is attached to the other end of the C-shaped arm.

As a size of an imaging region is limited by a size of an X-ray detector, it is often impossible to obtain a volumetric image for an elongated object or region of interest of the object using only one single image acquisition scan.

In particular, this is an issue during interventional procedures, in which a three-dimensional image volume is reconstructed from a plurality of two-dimensional X-ray projection images of an object to be examined, which projection images are acquired in a rotational scan in which the C-arm rotates about the patient, for example over a 180 degree angle.

An acquisition, using a C-arm system, of a 3D image volume data representing a relatively large region of interest can be improved.

SUMMARY OF THE INVENTION

Hence, there may be a need to provide an imaging system for imaging an elongated region of interest of an object, which eases a combination of 2D scans into a 3D image volume for a C-arm system.

The problem of the present invention is solved by the subject-matters of the independent claims, wherein further embodiments are incorporated in the dependent claims. It should be noted that the aspects of the invention described in the following apply also to the imaging system for imaging an elongated region of interest of an object, the imaging method for imaging an elongated region of interest of an object, the computer program element, and the computer readable medium.

According to the present invention, an imaging system for imaging an elongated region of interest of an object is presented. The imaging system comprises an acquisition unit and a processing unit.

The acquisition unit is a C-arm acquisition unit and configured to acquire first image data of the object to be imaged in a first rotational scan with a first geometric imaging parameter. That is, the first image data comprise a series of X-ray projection images acquired during a rotational scan of the C-arm using the first geometric imaging parameter.

The acquisition unit is further configured to acquire second image data of an object to be imaged in a second rotational scan with a second, different geometric imaging parameter. That is, the first image data comprise a series of X-ray projection images acquired during a rotational scan of the C-arm using a different geometric imaging parameter.

The processing unit is configured to combine the first and second image data into volume data.

The second geometric imaging parameter may be defined based on object specific data so as to align the volume data with to the elongated region of interest of the object to be imaged. Preferably, further geometric imaging parameters to be used in further rotational scans may be defined in a similar manner. The defining of the parameters may be performed manually or (semi)automatically. For example, based on the object specific data, a processing unit may automatically determine geometric imaging parameters for the individual rotational scans.

Exemplarily and in other words, a large volume imaging system using a C-arm is provided, whereby the rotational scan imaging can be adapted to object specific data, as e.g. anatomy data. The large volumes or the elongated region of interest can be e.g. a spine, an abdominal aorta, a lung, or other organs which are larger than the imaging system's field of view along an object or patient axis.

The imaging parameters can be defined in view of having sufficient anatomy coverage with as few rotational C-arm scans as possible. This is achieved by adapting positioning and orientation of the imaging system's field of view to the anatomical region of interest. In other words, the field of view of the volumetric images reconstructed from the individual C-arm rotational scans may follow an e.g. curved and/or irregularly shaped region of interest. As a result, the data intake and thereby the dosage and the duration of data processing is reduced. In summary, the combination of 2D scans into a 3D image volume for a C-arm system is facilitated.

Combining first and second image data into volume data can be understood:

as stitching together different first and second 2D image data to 2D image data and then reconstructing the 2D image data to 3D volume data or as reconstructing different first and second 2D image data to different first and second 3D volume data and then stitching the different first and second 3D volume data together to 3D volume data.

In other words, the reconstruction of the volume data can be performed independently for each volume or by combining projection data from subsequent scans in the case of overlapping voxels. In an example, the combination into volume data is performed by transferring first image data into first sub-volume data, transferring second image data into second sub-volume data, and fusing the first and second sub-volume data into volume data.

In another example, the combination into volume data is performed by fusing first and second image data to extended image data and transferring the extended image data into volume data. The fusing of the first and second image data to extended image data may be based on image registration. In particular in case that the reconstruction is performed for each scan separately and the position of the C-arm system along the patient axis is not known with high accuracy, image based registration can be used to fuse the first and second image data to extended image data. The registration can also be made by a phantom measured together with the first and second image data.

Object specific data may be used as basis to define the imaging parameters for the second rotational scan and, optionally, for the first rotational scan and/or further rotational scans. The object specific data is preferably patient specific scan planning data such as a pre-interventional MR/CT data set. Alternatively or in addition, the object specific data may include a surface model generated by an optical camera system and/or an X-ray projection set acquired in a scanogram mode.

The different first and second geometric imaging parameters can be distinguished by different sizes of the field of view. In detail, the size of the field of view can be adapted to the size of the region of interest in the object's anatomy for each imaging parameter based on object specific data. The adaption of the sizes of the field of view can be e.g. made by collimators, which reduce the field of view and thereby the reconstructed volume.

The different first and second geometric imaging parameters may include an isocenter position, an orientation of the acquisition unit, an orientation of its X-ray detector or combinations thereof. In detail:

In an example, the first imaging parameter is a first isocenter position. The second imaging parameter is a second isocenter position. The first and second isocenter positions represent the positions of an isocenter in the first and second rotational C-arm scans. Between the scans, the isocenters may be displaced relative to each other in a direction different to a scanning direction of the imaging system to adapt a position of image acquisition to a region of interest. The scanning direction may be e.g. along a spine. The first and second isocenter positions may be displaced relative to each other in a direction normal or different to the scanning direction of the imaging system. The scanning direction may extend along the longitudinal direction of the elongated region of interest.

The isocenter positions variable between a first and second isocenter position can be e.g. achieved via a variation of an object support or table height or a positioning or corresponding repositioning of the C-arm acquisition unit. In detail:

The first and second isocenter positions may differ by at least one of the group of:
height of the object support,
longitudinal position of the object support relative to a longitudinal direction of the object,
lateral position of the object support relative to a lateral direction of the object,
position of the C-arm of the acquisition unit, or
a combination thereof.

In a further example, an orientation of the C-arm acquisition unit may vary between the first rotational scan and the second rotational scan. The variable first and second orientations can be e.g. achieved via a tilt of the entire acquisition unit or a tilt of its X-ray detector. First and second image data acquired in rotational sans using the first and second orientation of the C-arm acquisition unit can be combined into 3D volume data to cover a larger volume by first stitching or first reconstructing as explained above.

In particular, the first imaging parameter may be a first orientation of a rotational plane of the C-arm acquisition unit. The second imaging parameter may be a second orientation of the rotational plane of the C-arm acquisition unit. The first and second orientations may be rotated relative to each other to adapt an orientation of image acquisition to the region of interest. That is, the rotational planes, in which the first and second rotational scans are carried out, may be tilted with respect to each other. The variable first and second orientations, e.g. achieved via a tilt of the acquisition unit, can differ by an angle between 1° and 90°, preferably between 5° and 75°, and more preferably between 10° and 45°.

In an example, the acquisition unit comprises an X-ray detector, which is configured to rotate between the first and the second orientation. Then, the first imaging parameter is a first orientation of the X-ray detector and the second imaging parameter is a second orientation of the X-ray detector. The X-ray detector may be configured to rotate between landscape or portrait mode as first and second orientations. This rotation between landscape or portrait mode amounts to about 90°. In this way, larger coverage along the object's or patient's axis is exchanged with larger coverage in a plane of rotation.

As stated above, the different first and second geometric imaging parameters can also be distinguished from each other by combinations of different isocenter positions, different orientations of the acquisition unit or different orientations of its X-ray detector. For example, an acquisition with shifted isocenter and shifted tilt or orientation of the acquisition unit is possible, or an acquisition with shifted isocenter and shifted orientation or mode (landscape and portrait) of the X-ray detector is possible.

The field of views or regions of the first and second image data can be arranged next to each other with a small overlap. To further reduce the patient's dosage, the overlap can be reduced to be only present in conical sub-volumes of the reconstructed field of view. Conical subvolumes may occur at lateral ends of a truncated field of a C-arm system.

Object specific data are used as basis to define the first and second geometric imaging parameters. The object specific data can be patient specific scan planning data, based on which the imaging system can carry out two or more rotational acquisition scans for maging an elongated region of interest of an object. In detail, geometric imaging parameters for the individual scans, in particular the isocenter positions, the acquisition unit orientations or angulations, or the X-ray detector orientations or modes (portrait, landscape) can be optimally selected based on the object specific data.

In an embodiment, object specific data such as scan planning data may be determined from a pre-interventional MR or CT image data set. For example, an elongated region of interest may be segmented in such data set either manually or in a (semi)automatic manner. Based on this region of interest, geometric imaging parameters for two or more rotational C-arm scans may be automatically selected, so as to obtain a volumetric image of the elongated region of interest using a C-arm acquisition unit. Preferably, the parameters are selected so as to optimally align a volumetric image that is fused and reconstructed from the individual rotational scans with the region of interest. That is, the reconstructed volume preferably covers substantially the entire region of interest while keeping a radiation dose received by the patient to a minimum.

According to the present invention, also an imaging method for imaging an elongated region of interest of an object is presented. It comprises the following steps, not necessarily in this order:

acquiring first image data of the object to be imaged with a first imaging parameter of a C-arm acquisition unit, acquiring second image data of the object to be imaged with a second imaging parameter of the C-arm acquisition unit, wherein the second geometric imaging parameter is defined based on object specific data for the volume data to be aligned with the elongated region of interest of the object to be imaged, and combining the first and second image data into volume data.

The object specific data can be patient specific anatomic data.

The different first and second geometric imaging parameters can be distinguished by an isocenter position, an orientation of the acquisition unit, an orientation of its X-ray detector or combinations thereof.

Combining first and second image data into volume data can be understood as stitching together different first and second 2D image data to 2D image data and then reconstructing the 2D image data to 3D volume data or as reconstructing different first and second 2D image data to different first and second 3D volume data and then stitching the different first and second 3D volume data together to 3D volume data.

According to the present invention, also a computer program element is presented, wherein the computer program element comprises program code means for causing the imaging system as defined in the independent claim to carry out the steps of the imaging method as defined in the independent claim when the computer program is run on a computer controlling the imaging system.

It shall be understood that the imaging system, the imaging method, the computer program element for controlling such system and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
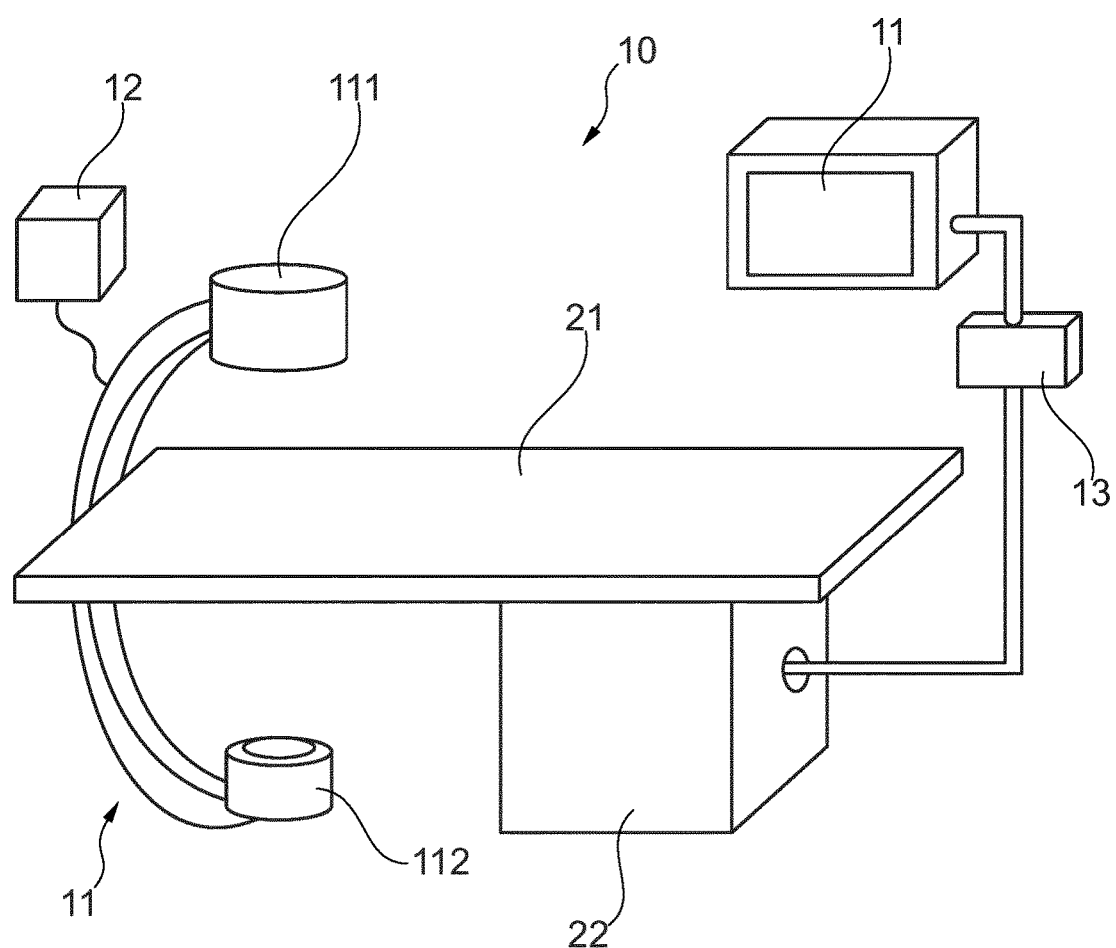
FIG. 1 shows a schematic drawing of an example of an imaging system for imaging an elongated region of interest of an object.

FIG. 1 shows schematically and exemplarily an embodiment of an imaging system 10 for imaging an elongated region of interest of an object. The elongated region of interest can be e.g. a spine, an abdominal aorta, a lung, or other organs which are larger than the imaging system's field of view along an object or patient axis.

The imaging system 10 comprises an acquisition unit 11 and a processing unit 13. The acquisition unit 11 is a C-arm acquisition unit and comprises an X-ray source 111 and an X-ray detector 112. The imaging system 10 further comprises an interface unit 14, here in form of a display, to provide information and control to a user.

A patient table 21 is arranged to place an object or patient to be examined (not shown) between the X-ray source 111 and the X-ray detector 112. The C-arm is provided such that a movement of the C-arm around the object is possible to be able to adapt the viewing direction. Further, a base 22 is provided on which the patient table 21 is mounted on a floor of an examination room.

The C-arm acquisition unit 11 is configured to acquire first image data of the object to be imaged in a first rotational scan with a first geometric imaging parameter, optionally defined based on object specific data. The acquisition unit 11 is further configured to acquire second image data of an object to be imaged in a second rotational scan with a second, different geometric imaging parameter defined based on object specific data. At least the second geometric imaging parameter is defined based on object specific data for the volume data to be aligned with or to correspond to the elongated region of interest of the object to be imaged. The processing unit 13 is configured to combine the first and second image data into volume data.

Figure 2:
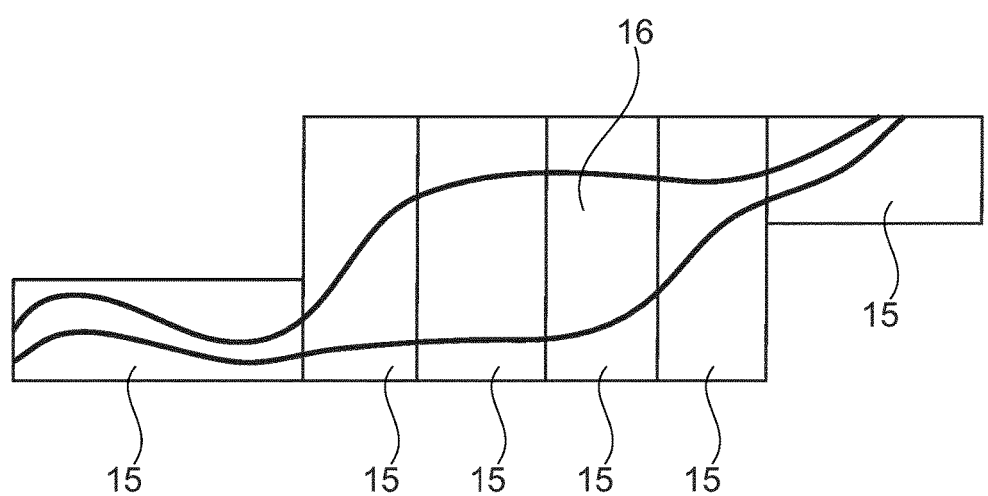
FIG. 2 shows schematically and exemplarily an adaption of an imaging system to object specific data.

As shown in FIG. 2, the imaging by the C-arm acquisition unit 11 can be adapted to object specific data, as e.g. anatomy data. In other words, the single fields of view 15 may follow a here curved region of interest 16. This is achieved by adapting positioning and orientation of the imaging system's field of view 15 to the anatomical region of interest 16. Thereby, as less scans as possible are done for sufficient anatomy coverage. As a result, the data intake and thereby the dosage and the duration of data processing is reduced.

Figure 3:
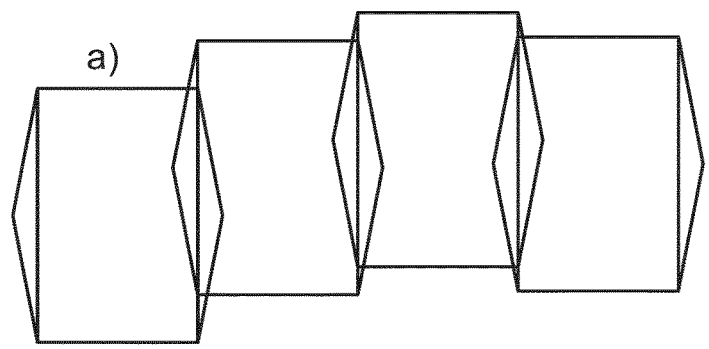
FIG. 3 shows schematically and exemplarily different geometric imaging parameters for the imaging system according to the invention.
Figure 3:
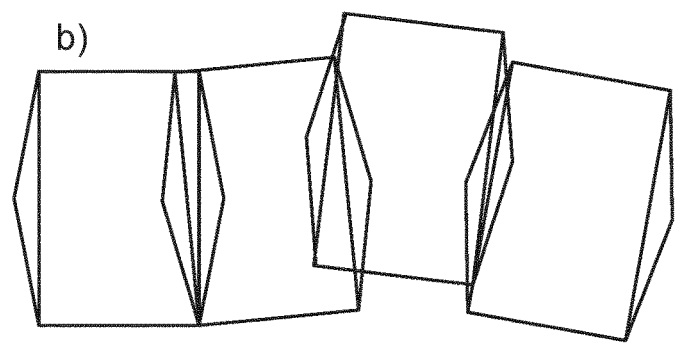
Figure 3:
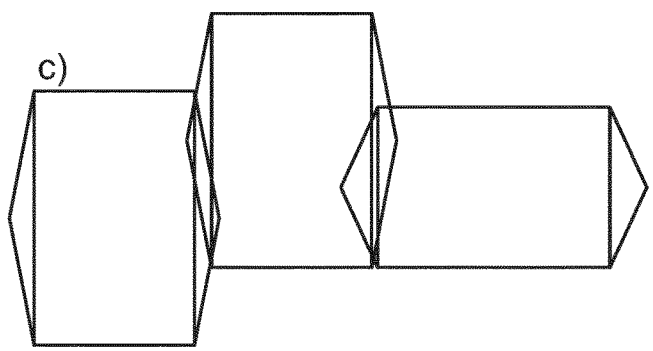

Object specific data used as basis to define the first and second imaging parameters can be patient specific scan planning data as e.g. a pre-interventional MR/CT data set, or in addition or alternatively a surface model generated by an optical camera system, an X-ray projection set acquired in a CT scanogram mode or a combination thereof. The processing unit 13 may be configured to combine the first and/or second image data and/or the volume data with object specific data. In other words, when object specific data are available, the imaging system 10 can carry out two or more rotational acquisition scans for imaging an elongated region of interest of an object based on these data. In detail, geometric imaging parameters for two or more rotational C-arm scans e.g. the isocenter positions, the acquisition unit's orientations or angulations, or the X-ray detector 112 orientations or modes (portrait, landscape) can be optimally selected based on the object specific data, so as to obtain a volumetric image of the elongated region of interest. Preferably, the parameters are selected so as to optimally align a volumetric image that is fused and reconstructed from individual rotational scans of a C-arm acquisition unit with the region of intere As shown in FIG. 3, the different geometric imaging parameters, that is the different rotational scans, can be distinguished by an isocenter position, an orientation of the acquisition unit 11, an orientation of its X-ray detector 112 or combinations thereof.

According to FIG. 3a, for the first imaging parameter, the acquisition unit 11 acquires first image data in a rotational scan having a first isocenter position. For the second imaging parameter, the acquisition unit 11 acquires second image data with a rotational scan having a second isocenter position. The first and second isocenter positions are displaced relative to each other in a direction different to an acquisition direction of the imaging system 10 to adapt a position of image acquisition to a region of interest. The acquisition direction may be e.g. along a spine and the first and second isocenter positions are here displaced relative to each other in a direction normal to the acquisition direction. The same applies for the third and fourth imaging parameters shown in FIG. 3a.

The isocenter positions variable between a first and second isocenter position can be e.g. achieved via a variation of an object support or table height or a positioning or corresponding repositioning of the C-arm acquisition unit 11. In detail, the first and second isocenter positions may differ by at least one of the group of height of the object support, longitudinal position of the object support relative to a longitudinal direction of the object, lateral position of the object support relative to a lateral direction of the object, position of the C-arm of the acquisition unit 11, or a combination thereof.

The variable first and second orientations can be e.g. achieved via a tilt of the entire acquisition unit 11 or a tilt of its X-ray detector 112.

According to FIG. 3b, a rotational plane of the C-arm acquisition unit 11 tilts between the first and the second orientation. With the first imaging parameter, the acquisition unit 11 acquires first image data with a first orientation of the rotational scan plane. With the second imaging parameter, the acquisition unit 11 acquires second image data with a different second orientation of the rotational scan plane. The first and second orientations are tilted at an angle with respect to each other to adapt an orientation of image acquisition to a region of interest. In FIG. 3b, for the third rotational scan, the acquisition unit 11 acquires third image data with a combination of a different third orientation and a different isocenter position compared to the first and second imaging parameters. For the fourth rotational scan, the acquisition unit 11 acquires fourth image data with a combination of another different fourth orientation and another a different isocenter position compared to the previous imaging parameter.

According to FIG. 3c, with the first imaging parameter, the acquisition unit 11 acquires first image data with a first isocenter position. With the second imaging parameter, the acquisition unit 11 acquires second image data with a second isocenter position. With the third imaging parameter, the X-ray detector 112 of the acquisition unit 11 rotates from a portrait to a landscape mode or orientation. This rotation between landscape or portrait mode amounts to 90°.

In FIGS. 3a to 3c, the field of views of image data acquired in a plurality of rotational scans are arranged next to each other. Between the scans, the acquisition unit (or alternatively the patient support) is moved in a scanning direction so that there is a small overlap substantially only in conical sub-volumes of the reconstructed field of view for each scan.

Combining image data into volume data can be understood as either stitching together different first and second 2D image data to 2D image data and then reconstructing the 2D image data to 3D volume data or as reconstructing different first and second 2D image data to different first and second 3D volume data and then stitching the different first and second 3D volume data together to 3D volume data.

Figure 4:
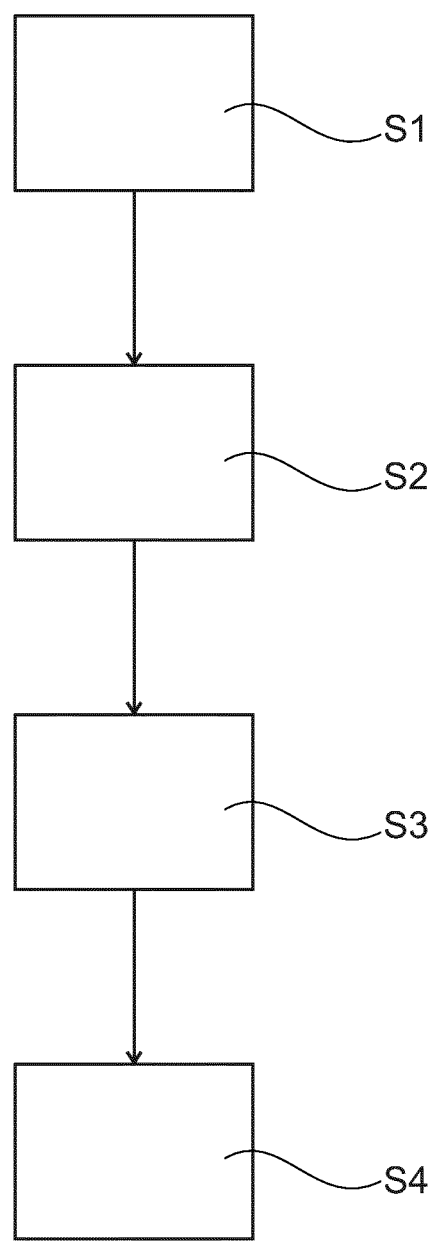
FIG. 4 shows basic steps of an example of an imaging method for imaging an elongated region of interest of an object.

FIG. 4 shows a schematic overview of steps of an imaging method for imaging an elongated region of interest of an object. The imaging method comprises the following steps, not necessarily in this order:

In a first step S1, acquiring first image data of the object to be imaged in a rotational scan with a first geometric imaging parameter of a C-arm acquisition unit 11.

In a second step S2, acquiring second image data of the object to be imaged in a rotational scan with a second geometric imaging parameter of the C-arm acquisition unit 11, wherein at least the second, different imaging parameter is defined based on object specific data to be aligned with the elongated region of interest of the object to be imaged.

In a third step S3, combining the first and second image data into volume data.

The object specific data can be patient specific anatomic data.

The different first and second imaging parameters can be distinguished by an isocenter position, an orientation of the acquisition unit 11, an orientation of its X-ray detector 112 or combinations thereof.

Combining first and second image data into volume data can be understood as stitching together different first and second 2D image data to 2D image data and then reconstructing the 2D image data to 3D volume data or as reconstructing different first and second 2D image data to different first and second 3D volume data and then stitching the different first and second 3D volume data together to 3D volume data.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system for imaging an elongated region of interest of an object, comprising:
   a C-arm acquisition unit, and
   a processing unit,
   wherein the acquisition unit is configured to acquire first image data of the object to be imaged in a first rotational scan with a first geometric imaging parameter,
   wherein the acquisition unit is configured to acquire second image data of the object to be imaged in a second rotational scan with a second, different geometric imaging parameter,
   wherein the processing unit is configured to combine the first and second image data into volume data, and
   wherein the second geometric imaging parameter is definable based on object specific data so as to align the volume data with the elongated region of interest of the object to be imaged.

2. System according to claim 1, wherein the first imaging parameter comprises a first isocenter position of an isocenter in the first rotational scan, wherein the second imaging parameter comprises a second isocenter position of an isocenter in the second rotational scan, the first and second isocenter positions being displaced relative to each other in a direction different to a scanning direction of the imaging system, wherein the scanning direction extends along the longitudinal direction of the elongated region of interest.

3. System according to claim 1, wherein the first and second isocenter positions differ by at least one of the group of:
   height of an object support,
   longitudinal position of an object support relative to a longitudinal direction of the object,
   lateral position of the object support relative to a lateral direction of the object, or
   a position of a C-arm of the acquisition unit.

4. System according to claim 1, wherein the first imaging parameter is a first orientation of a rotational plane of the C-arm acquisition unit, wherein the second imaging parameter is a second orientation of the rotational plane, and wherein the first and second orientations are rotated relative to each other to adapt an orientation of image acquisition to the region of interest.

5. System according to claim 1, wherein the first imaging parameter is a first orientation of an X-ray detector of the acquisition unit, wherein the second imaging parameter is a second orientation of the X-ray detector, and wherein the first and second orientations are rotated relative to each other to adapt an orientation of image acquisition to the region of interest.

6. System according to claim 5, wherein the X-ray detector is configured to rotate between landscape or portrait as first and second orientations.

7. System according to claim 1, wherein the combination into volume data is performed by transferring first image data into first sub-volume data, transferring second image data into second sub-volume data, and fusing the first and second sub-volume data into volume data.

8. System according to claim 1, wherein the combination into volume data is performed by fusing first and second image data to extended image data and transferring the extended image data into volume data.

9. System according to claim 8, wherein the fusing of the first and second image data to extended image data is based on image registration.

10. System according to claim 1, wherein the processing unit is further configured to combine the first and/or second image data and/or the volume data with object specific data.

11. System according to claim 10, wherein the object specific data are at least one of the group of a pre-interventional MR/CT data set, a surface model generated by an optical camera system, an X-ray projection set acquired in a CT scanogram mode or a combination thereof.

12. An imaging method for imaging an elongated region of interest of an object, comprising the following steps:
   acquiring, in a first rotational scan, first image data of the object to be imaged with a first imaging parameter of a C-arm acquisition unit,
   acquiring, in a second rotational scan, second image data of the object to be imaged with a second, different imaging parameter of the C-arm acquisition unit, and combining the first and second image data into volume data,
   further comprising the step of defining the second imaging parameter based on object specific data so as to align the volume data with the elongated region of interest of the object to be imaged.

13. A computer program element for controlling a system, which, when being executed by a processing unit, is adapted to perform the method steps of claim 12.

14. A computer readable medium having stored the computer program element of claim 13.

\* \* \* \* \*